United States Patent [19]

Wilcox, Jr.

[11] Patent Number: Plant 7,523

[45] Date of Patent: May 14, 1991

[54] FORSYTHIA PLANT NAMED 'FIESTA'

[76] Inventor: Harry D. Wilcox, Jr., 133 Ayrshire La., Avon, Conn. 06001

[21] Appl. No.: 392,024

[22] Filed: Aug. 10, 1989

[51] Int. Cl.[5] ..... A01H 5/00

[52] U.S. Cl. ..... Plt./54

[58] Field of Search ..... Plt./54

*Primary Examiner*—James R. Feyrer

*Attorney, Agent, or Firm*—Fishman, Dionne & Cantor

[57] ABSTRACT

A new variety of Forsythia having distinctive variegated foliage a slower growth rate and a denser growth habit.

2 Drawing Sheets

1

The present invention relates to a new and distinct selection of Forsythia, named Forsythia cultivar *Forsythia×intermedia* 'Fiesta' which I discovered in a group of *Forsythia×intermedia* 'Lynwood' at Farmington Valley Nursery, 138 Waterville Road, Avon, Conn. in 1977.

Among the novel characteristics of this new variety which distinguish it from 'Lynwood' and from other varieties of which I am aware are:

(a) 'Fiesta' exhibits unusually attractive tricolor variegated foliage;

(b) 'Fiesta' exhibits unusually attractive pale yellow flowers;

(c) 'Fiesta' exhibits a slower growth rate than the 'Lynwood';

(d) 'Fiesta' has a spreading habit, in contrast to 'Lynwood' which has a vase habit that eventually weeps and 'Fiesta' has a shorter internode length than 'Lynwood'; and (e) The fall color of the foliage of 'Fiesta' lacks purple blotches which characterize the fall coloration of 'Lynwood'.

The blooming dates, blooming pattern, i.e. an equal distribution of flowers along the stem, bark and lentcels of 'Fiesta' are substantially the same as those of the 'Fiesta'.

There are no mature specimens of 'Fiesta' as of the filing of the present application. The above comparisons were made between two plants, i.e.:

a specimen of *Forsythia×intermedia* 'Lynwood' and a periclinal chimera sport from a specimen of 'Lynwood', i.e. a specimen of 'Fiesta'. Each of the specimens was five years old and grown in a substantially identical root zone volume, i.e. a 2 gallon container. Each of the specimens was pruned annually and the comparisons are therefore based only on current growth.

The new variety 'Fiesta' has been propagated solely by taking cuttings. Mound or stool layering has not been used as a propagation technique. Seed set of 'Fiesta' has not been observed and it is not known whether 'Fiesta' produces viable pollen. Asexual reproduction of 'Fiesta' by cutting performed at Farmington Valley Nursery indicates that the foregoing and other distinguishing characteristics come true to form and are established and transmitted through successive propagations.

2

The accompanying drawings show a typical specimen of the new variety, depicted in color as nearly true as possible.

Figure 2:
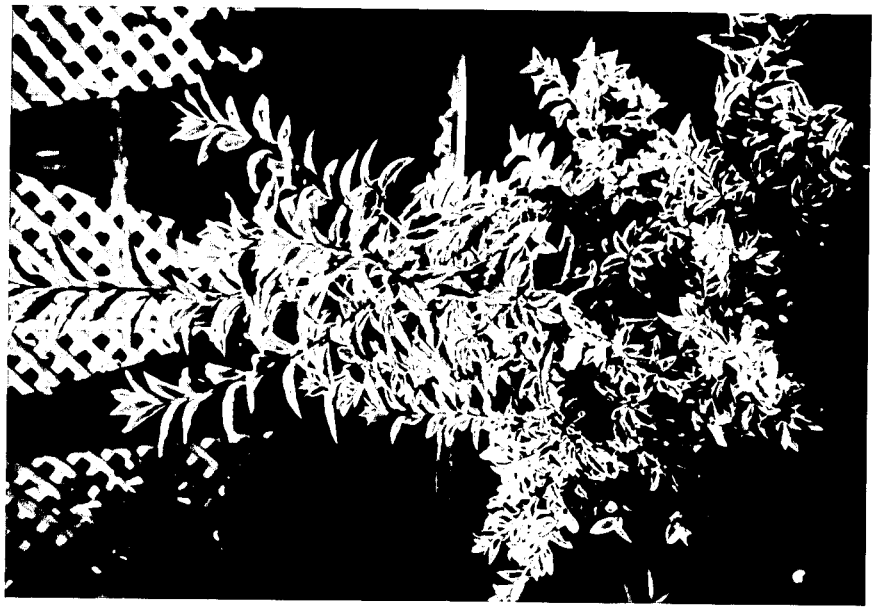
FIG. 2 shows the denser growth habit of the new variety.
Figure 1:
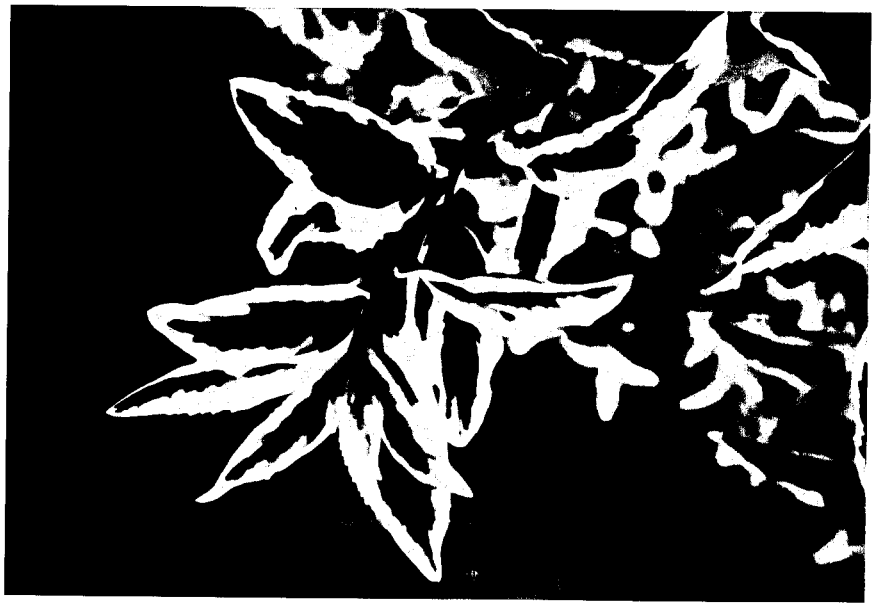
FIG. 1 shows the distinctive variegated foliage of the new variety.
Figure 3:
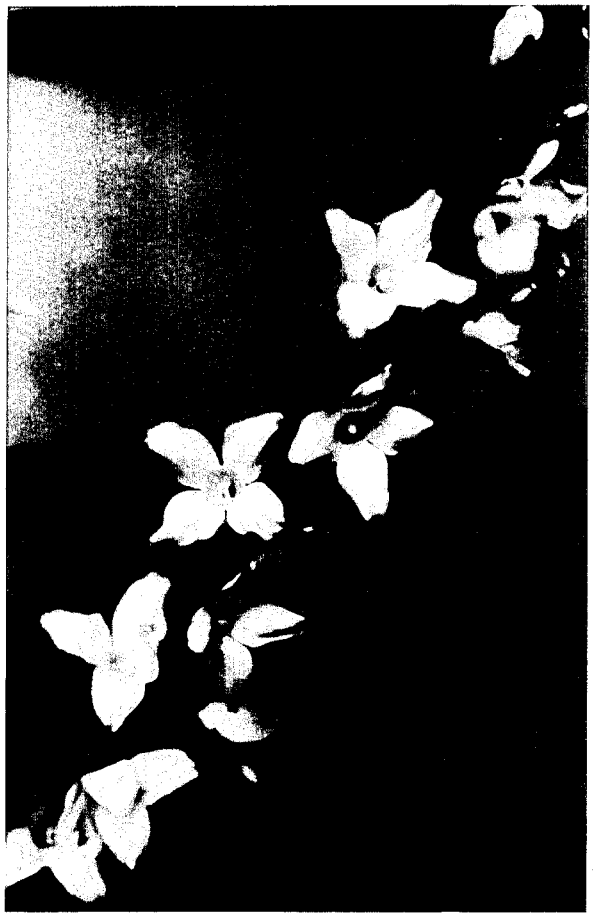
FIG. 3 shows the flower of the new variety.

Color terminology used herein is in accord with *The Horticultural Color Chart,* by Robert F. Wilson, Henry Stone & Son, Ltd, 1938 and refers to page and plate numbers in the aforementioned chart.

FLOWER

Blooming Habit

A. Bud:
1. *Size.*—2 mm at base, 3 mm long.
2. *Form.*—Superposed with auxiliary bud set.
3. *Color.*—Light tan at base of scale, to dark brown at tip.
4. *Sepals.*—7 mm, pale white with a green stripe.
5. *Peduncle.*—Calyx deeply 4 lobed, persistant.

B. Bloom:
1. *Size.*—Approximately 2–3 cm.
2. *Borne.*—1–6.
3. *Form.*—Perfect.
4. *Petalage.*—4 petals.
5. *Color.*—Chrome yellow (light), page 93, plate 605/1 to sulfur yellow, page 1, plate #1/3.

C. Petals:
1. *Form.*—Oblong.
2. *Arrangement.*—4.
3. *Persistence.*—2–3 weeks.
4. *Fragrance.*—Scentless.

PLANT

A. Overall size and habit:
1. *Internodal length.*—2.2 cm.

B. Foliage
1. *Shape.*—Ovate-oblong to oblong lanceolate.
2. *Base.*—Acute to rounded.
3. *Tip.*—Acute.
4. *Margins.*—Serrate upper one-half.
5. *Width.*—2.4 to 4.1 cm.
6. *Length.*—4.4 to 7.1 cm.
7. *Arrangement.*—Opposite.
8. *Color.*—The leaves are variegated and exhibit three distinct hues: (i) The central portion of the leaf is colored spinach green, page 187, plate

#$09^{60}$. (ii) The margins of the leaf are colored yellow. The intensity of the yellow color varies with intensity of illumination. The brightest hue exhibited is sulphur yellow, page 1, plate 1/3. The yellow color of the margins in lower intensity light are graduated tints of Barium yellow, page 131, plate #s $50^{3/3}$, $50^{3/2}$ and $50^{3/1}$. (iii) Patches of pod green, plate 120, plate #$0^{61/1}$ are present between the central portion of the leaf and the leaf margin where a layer of yellow mesophyll overlaps a layer of green mesophyll. Trifoliate leaves do not appear.

I claim:

1. A new and distinct variety of Forsythia as substantially shown and described herein, that is characterized particularly as a novelty by the unique combination of distinct foliage construction, pale yellow flowers, slow growth rate, reduced internodal length and a denser branching habit.

* * * * *